(12) United States Patent
Onda et al.

(10) Patent No.: US 8,772,539 B2
(45) Date of Patent: Jul. 8, 2014

(54) METHOD FOR SYNTHESIZING UNSATURATED CARBOXYLIC ACID AND/OR DERIVATIVE OF SAME

(75) Inventors: Ayumu Onda, Kochi (JP); Yumiko Matsuura, Kochi (JP); Kazumichi Yanagisawa, Kochi (JP)

(73) Assignees: Kabushiki Kaisha Sangi, Tokyo (JP); Kochi University, Kochi (JP)

( * ) Notice: Subject to any disclaimer, the term of this patent is extended or adjusted under 35 U.S.C. 154(b) by 57 days.

(21) Appl. No.: 13/503,780

(22) PCT Filed: Oct. 25, 2010

(86) PCT No.: PCT/JP2010/006295
§ 371 (c)(1),
(2), (4) Date: May 8, 2012

(87) PCT Pub. No.: WO2011/052178
PCT Pub. Date: May 5, 2011

(65) Prior Publication Data
US 2012/0277467 A1    Nov. 1, 2012

(30) Foreign Application Priority Data
Oct. 29, 2009    (JP) .................. 2009-249427

(51) Int. Cl.
C07B 35/00    (2006.01)
C07C 51/347    (2006.01)

(52) U.S. Cl.
CPC .................. *C07C 51/347* (2013.01)
USPC ....................................... 562/599

(58) Field of Classification Search
CPC combination set(s) only.
See application file for complete search history.

(56) References Cited

U.S. PATENT DOCUMENTS

| | | | | |
|---|---|---|---|---|
| 2,859,240 A | * | 11/1958 | Holmen | 560/212 |
| 4,729,978 A | * | 3/1988 | Sawicki | 502/174 |
| 5,252,473 A | | 10/1993 | Walkup et al. | |
| 6,323,383 B1 | | 11/2001 | Tsuchida et al. | |
| 2009/0076297 A1 | | 3/2009 | Bogan, Jr. et al. | |
| 2013/0071893 A1 | * | 3/2013 | Lynch et al. | 435/136 |

FOREIGN PATENT DOCUMENTS

| | | | |
|---|---|---|---|
| JP | 63023744 | * | 2/1988 |
| JP | 2004-115480 | | 4/2004 |
| JP | 2006-015330 | | 1/2006 |

(Continued)

OTHER PUBLICATIONS

Database CAPLUS Chemical Abstracts Service, Columbus, Ohio, US; Database Accession No. 1965:90338, Abstract of SU 152237, Ustavshchikov et al. Feb. 18, 1965.*

(Continued)

*Primary Examiner* — Karl J Puttlitz
(74) *Attorney, Agent, or Firm* — Kenneth H. Sonnenfeld; Margaret B. Brivanlou; King & Salding LLP

(57) ABSTRACT

An appropriate catalyst is found for synthesis of an unsaturated carboxylic acid and/or a derivative thereof using as a raw material compound a hydroxycarboxylic acid and/or a derivative thereof that can easily be synthesized from a polysaccharide such as biomass-derived cellulose, and an efficient method for synthesizing the unsaturated carboxylic acid and/or the derivative thereof is provided. This method is a method for synthesizing an unsaturated carboxylic acid and/or a derivative thereof, wherein an apatite compound is used as a catalyst to synthesize the unsaturated carboxylic acid and/or the derivative thereof from a biomass-derived hydroxycarboxylic acid and/or a derivative thereof by a dehydration reaction.

4 Claims, 2 Drawing Sheets

(56) References Cited

FOREIGN PATENT DOCUMENTS

| | | |
|---|---|---|
| JP | 2009-067775 | 4/2009 |
| JP | 2009-201405 | 9/2009 |
| WO | WO 99/38822 | 8/1999 |

OTHER PUBLICATIONS

Database CAPLUS Chemical Abstracts Service, Columbus, Ohio, US; Database Accession No. 2008:1393602, Abstract of Tacke, DGMK Tagungsbericht (2008), Mar. 2008(Preprints of the DGMK-Conference "Future Feedstocks for Fuels and Chemicals", 2008), 81-88.*

Database CAPLUS Chemical Abstracts Service, Columbus, Ohio, US; Database Accession No. 2009:1103231, Abstract of Fan et al., Catalysis Reviews—Science and Engineering (2009), 51(3), 293-324.*

Database CAPLUS Chemical Abstracts Service, Columbus, Ohio, US; Database Accession No. 2012:413068, Abstract of KR 2012025888, Korea Research Institute of Chemical Technology, S. Korea, Hong et al., Mar. 16, 2012.*

Yumiko Matsuura et al., "Hydroxyapatite Shokubai ni yoru Nyusan Kara Acryl-san eno Dassui Hanno," Dai 106 Kai CatSJ Meeting Toronkai A Yokoshu, p. 159, Sep. 15, 2010, cited as a "P,A" reference in the International Search Report for PCT/JP2010/006295.

Kabushiki Kaisha Sangi and Kochi University, International Search Report for PCT/JP2010/006295, Nov. 16, 2010, 2 pages.

European Search Report for European Patent Application No. 10826314.6, in the name of Kabushiki Kaisha Sangi et al., Mar. 28, 2013, 6 pages.

* cited by examiner

METHOD FOR SYNTHESIZING UNSATURATED CARBOXYLIC ACID AND/OR DERIVATIVE OF SAME

TECHNICAL FIELD

The present invention relates to a method for synthesizing an unsaturated carboxylic acid and/or a derivative thereof from a hydroxycarboxylic acid and/or a derivative thereof using an apatite compound as a catalyst.

BACKGROUND ART

Acrylic acid is a raw material monomer for polyacrylic acids or acrylic acid-based copolymers. With increase in the amount of water-absorbing resins (polysodium acrylate) used, its production amount is increasing. The acrylic acid is usually manufactured by synthesizing acrolein from propylene, which is a petroleum-derived raw material, and subjecting the acrolein to catalytic gas phase oxidation to be converted into an acrylic acid (for example, patent document 1).

However, there is a concern that the petroleum-derived raw materials will be depleted in future. From such reasons, studies have been made aimed at obtaining an unsaturated carboxylic acid from biomass. For example, a method for synthesizing an unsaturated carboxylic acid or an ester thereof from an ammonium salt of a hydroxycarboxylic acid is disclosed in patent document 2.

PRIOR ART DOCUMENTS

Patent Documents

Patent Document 1: Japanese unexamined Patent Application Publication No. 2006-15330
Patent Document 2: Japanese unexamined Patent Application Publication No. 2009-67775

SUMMARY OF THE INVENTION

Object to be Solved by the Invention

However, in the method described in the above patent document 2, there are complicated steps such as requiring the separation of the ammonium salt of a hydroxycarboxylic acid into a hydroxycarboxylic acid and a non-aqueous ammonium cation-containing exchange resin.

Therefore, it has been an object of the present invention to more easily synthesize an unsaturated carboxylic acid such as acrylic acid, or a derivative thereof such as a salt or ester, from a biomass-derived compound. More specifically, it has been an object to find an appropriate catalyst for synthesis of an unsaturated carboxylic acid such as acrylic acid and/or a derivative thereof using as a raw material compound a hydroxycarboxylic acid such as lactic acid and/or a derivative thereof that can easily be synthesized from a polysaccharide such as biomass-derived cellulose, and provide an efficient unsaturated carboxylic acid and/or a derivative thereof.

Means to Solve the Object

The present invention that could solve the above object is a method for synthesizing an unsaturated carboxylic acid and/or a derivative thereof, wherein an apatite compound is used as a catalyst to synthesize the unsaturated carboxylic acid and/or the derivative thereof from a biomass-derived hydroxycarboxylic acid and/or a derivative thereof by a dehydration reaction. Herein, the derivatives include salts or esters.

As the apatite compound, a compound comprising Ca and P is preferably used, a hydroxyapatite having a molar ratio of Ca to P of 1.5 to 1.8 is more preferably used, and as the hydroxyapatite, $Ca_{10}(PO_4)_6(OH)_2$ is most preferably used.

In addition, an aspect wherein the hydroxycarboxylic acid is lactic acid and the unsaturated carboxylic acid is acrylic acid is most preferable.

Effect of the Invention

According to the method of the present invention, it has become possible to synthesize an unsaturated carboxylic acid and/or a derivative thereof from a biomass-derived hydroxycarboxylic acid and/or a derivative thereof with a good yield over a long time period, by using as a catalyst an apatite compound that can easily be synthesized.

MODE OF CARRYING OUT THE INVENTION

Figure 1:
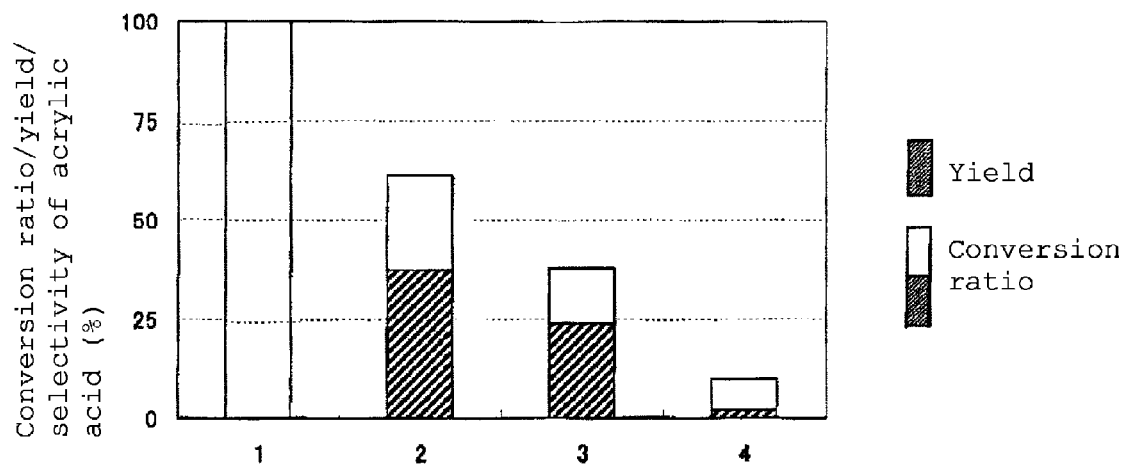
FIG. 1 shows the relationship between constituent elements of catalysts, and the conversion ratio from lactic acid to acrylic acid and yield.

In the present invention, a hydroxycarboxylic acid such as biomass-derived lactic acid is used as a raw material of an unsaturated carboxylic acid such as acrylic acid. The term biomass is generally used as a term that means a broad concept including foods, materials, and fuels consisting of biogenic substances, and those treated as industrial wastes are also included therein. They are, for example, rice straws, coconut shells, rice hulls, thinned wood, wood chip dust, pruned branches, and the like. The main component of these biomasses is cellulose, and the biomasses are not suitable for a food for humans who do not have the digestive enzymes for the cellulose. In addition, they are difficult to use as a fuel because they are not so excellent in combustion efficiency as petroleum components. Accordingly, at present there is no way other than disposal or incineration for these biomasses, and therefore, promotion of the effective use of them is extremely meaningful in terms of reducing the industrial wastes.

The present invention has focused on lactic acid that can easily be obtained from a polysaccharide such as cellulose or a monosaccharide abundantly comprised in the biomass. For example, a polysaccharide can be converted into glucose by an enzymatic method, a sulfuric acid method, a solid catalyst method, an ionic liquid method, and the like. For a method for manufacturing glucose from poly-glucose by the present applicants, an application for patent has been filed, as Japanese Unexamined Patent Application Publication No. 2009-201405. In addition, glucose can be converted into lactic acid by using a fermentation method, an alkali aqueous solution method, a solid catalyst method, and the like. In the present invention, the acrylic acid is synthesized from this lactic acid. Likewise, in the present invention, an acrylic acid ester can be synthesized from a lactic acid ester. In addition, in the present invention, the unsaturated carboxylic acid and the salt or ester thereof can be synthesized from a hydroxycarboxylic acid other than lactic acid, and a salt or ester thereof. In the following description, salts and esters are together referred to as "derivative thereof," and for simplicity, unless otherwise stated, the hydroxycarboxylic acid and the derivative thereof are referred to as simply hydroxycarboxylic acid, and the unsaturated carboxylic acid and the derivative thereof are referred to as simply unsaturated carboxylic acid. In addition, as for the hydroxycarboxylic acid ester, a biomass-derived hydroxycarboxylic acid may be reacted with a corresponding alcohol using a known esterification catalyst and the like, by a known method.

In the present invention, for the reaction of dehydration of hydroxycarboxylic acid to be converted into a corresponding unsaturated carboxylic acid, an apatite compound is used as a catalyst. The apatite compound in the present invention is a compound having an apatite structure, conceptually also includes a solid solution, and can be represented by the formula: $M_a(M'O_b)_cX_2$. M represents Ca, Sr, Pb, Mg, Cd, Fe, Co, Ni, Cu, Zn, La, H, and the like, and may be one or two or more types of them. Among these, an apatite compound in which M is Ca alone, or an apatite compound in which M is a combination of Ca and other elements, is preferable. In addition, M' represents P, V, As, C, S, and the like, and among these, an apatite compound in which M' is P alone, or an apatite compound in which M' is a combination of P and other elements, is preferable. X represents OH, F, Cl, or the like. $M_{10}(M'O_4)_6X_2$, in which a is 10, b is 4, c is 6, and a/c is 1.67, is the basic apatite compound. In the case of solid solution, or in the case where a/c deviates from 1.67, in the case where M includes an element that is not divalent, or in the case where M' includes an element that is not pentavalent such as C or S, the chemical formula is different from that of the above basic apatite compound. a/c may vary between 1.5 and 1.8. Note that in the case where M or M' is a combination of two or more types of elements, a or c is the total of the valences of each element. The most typical apatite is $Ca_{10}(PO_4)_6(OH)_2$ having a molar ratio of a/c (Ca/P) of 1.67.

For synthesis of the apatite compound, examples of Ca source include calcium nitrate, examples of Sr source include strontium nitrate, examples of P source include diphosphorus pentoxide ($P_2O_5$), examples of Pb source include lead nitrate, and examples of V source include vanadium pentoxide ($V_2O_5$). In addition, acetates, chlorides, metal complexes, carbonates, and the like can also be used. Also, in the case of synthesizing an apatite compound having other elements, it can be synthesized appropriately from these compounds.

The apatite compound can be synthesized, for example, in the presence of an alkali, by a hydrothermal reaction. The hydrothermal reaction may be performed by mixing aqueous solutions of raw material compounds which are made alkaline with NaOH and the like, at approximately 50 to 300° C. and at a pressure of approximately $1\times10^5$ to $1\times10^7$ Pa. Changing the above a/c can be achieved either by changing the ratio of the amount of raw material compounds used, or by adjusting the concentration of alkali. In addition, the apatite compound can be synthesized by a dry solid phase reaction method, a wet precipitation reaction method, or the like.

The form of the apatite compound may be granular, acicular, a ground product, one shaped into tablets, a honeycomb, or the like, and is not particularly limited. In addition, the apatite compound may be used as supported on a known support such as alumina and silica. The amount of apatite compound used can appropriately be selected considering reaction time.

Examples of the hydroxycarboxylic acid used as a raw material compound for the synthesis reaction of the present invention include lactic acid, citric acid, 3-hydroxypropionic acid, 3-hydroxy-2-methylpropionic acid, 3-hydroxybutanoic acid, 3-hydroxy-2-methylbutanoic acid, and 2,3-dimethyl-3-hydroxybutanoic acid. In addition, the derivatives thereof such as salts or esters can be used as a raw material compound.

The synthesis reaction of unsaturated carboxylic acid is preferably performed by bringing a hydroxycarboxylic acid aqueous solution in contact with the apatite compound. This is because it is possible to suppress condensation of hydroxycarboxylic acid before being introduced into a reaction tube, and in addition, when a reaction product is cooled with an ice bath trap or the like, it becomes an aqueous solution comprising an unsaturated carboxylic acid, which will easily be collected. However, the reaction proceeds even without a solvent. Reaction temperature is preferably 250 to 400° C. Reaction pressure may be any of a normal pressure, an increased pressure, or a reduced pressure, but the normal pressure is sufficient. The concentration of the hydroxycarboxylic acid aqueous solution is also not particularly limited, but considering the efficiency, it is preferably approximately 20 to 50% by mass. In addition, a solvent other than water may be comprised therein. In the case of hydroxycarboxylic acid, a hydrophilic organic solvent such as alcohol or ether may be used with or instead of water, and in addition, when the hydroxycarboxylic acid ester is difficult to dissolve or does not dissolve in water, the reaction may be performed without solvent, or an organic solvent that can dissolve the hydroxycarboxylic acid ester may be used.

As a mode of reaction, any of a fixed bed system, a moving bed system, a flow bed system, and the like can be adopted. An inert carrier gas such as nitrogen, argon, and helium can also be used. When a fixed-bed flow reactor is used, for example, an inert filler such as silica wool or quartz sand may be loaded upstream and downstream of an apatite compound layer.

The reaction products can be purified by known purification means (such as distillation or crystallization) to give a highly pure unsaturated carboxylic acid.

EXAMPLES

Hereinafter, the present invention will be described more specifically with referring to examples; however, the present invention is essentially not limited by the following examples, but can be carried out with appropriate modifications within the scope that can comply with the gist described above and below, and these are all included within the technical scope of the present invention.

Experimental Example 1

Effect of the Type of Catalyst

[Preparation of Apatite Compound]

1 mmol of $P_2O_5$ was dissolved in 7 ml of an aqueous solution comprising 7 mmol of NaOH, followed by addition of 8 ml of an aqueous solution comprising 3.33 mmol of calcium nitrate or strontium nitrate, to give two types of suspension. This suspension was introduced into an autoclave lined with polytetrafluoroethylene, and a hydrothermal treatment was performed at 110° C. and at a pressure of 143 kPa for 14 hours, while stirring. After the hydrothermal treatment, the obtained precipitates were well washed with water, and dried at 60° C. for 5 hours. $M_{10}(M'O_4)_6(OH)_2$ (M is Ca or Sr, and M' is P) in a powder state was obtained. This powder was shaped into pellets, which were then ground into a product having a size of approximately 250 to 500 μm, and the product thus obtained was used as a catalyst.

[Preparation of Catalyst Using Silica Gel]

1 mmol (based on P) of $P_2O_5$, or 1 mmol (based on Ca) of $CaNO_3$ was thoroughly dissolved in 1.5 ml of distilled water, and 1.0 g of silica gel (Fuji Silysia Chemical Ltd.; CARiACT (registered trademark) G-6; 30 to 200 mesh in particle diameter) was added thereto as a support, and then the mixture was stirred. The mixture was well stirred on a water bath until water was removed, and then dried overnight at 60° C. This powder was shaped into pellets, which were then ground into a product having a size of approximately 250 to 500 μm, and the product thus obtained was used as a catalyst.

[Preparation of Catalyst Using Active Carbon]

10 mmol (based on Na) of $NaNO_3$ was thoroughly dissolved in 1.5 ml of distilled water, and 1.0 g of active carbon (Wako Pure Chemical Industries, Ltd.; grade; mean particle diameter and the like) was added thereto as a support, and then the mixture was stirred. The mixture was well stirred on a water bath until water was removed, and then dried overnight at 60° C. This powder was shaped into pellets, which were then ground into a product having a size of approximately 250 to 500 μm, and the product thus obtained was used as a catalyst.

The five types of catalysts obtained above were used to perform a synthesis reaction of acrylic acid from lactic acid. The synthesis reaction was performed by using a fixed-bed flow reactor under atmospheric pressure. A reaction tube used was one made of Pyrex (registered trademark) glass and having an inner diameter of 7 mm. Quartz sand and silica wool were loaded upstream of the catalyst layer, and silica wool was loaded downstream thereof. Here, the amount of the catalyst used was basically set to 0.4 g in this experimental example.

For introduction of the lactic acid aqueous solution into the reaction tube, a microsyringe pump (AS ONE Corporation; model number MSPE-1) or a liquid chromatography pump (Hitachi, Ltd.; model number L-2420) was used. The concentration of the lactic acid aqueous solution was set to 38% by mass. The lactic acid aqueous solution was introduced into the catalyst layer at 20 μl/min, along with Ar as a carrier gas at 40 ml/min. The reaction temperature was set to 350° C. The liquid product was collected in an ice bath trap. In addition, the gaseous product was also collected from an outlet of the ice bath trap.

The liquid product was analyzed by high performance liquid chromatograph (HPLC), GC-MS, GC-FID, GC-TCD, and a total organic carbon analyzer, in addition to mass measurement by an electronic balance.

In HPLC, an LC-UV instrument (pump: 655, column oven: L-2350, detector: 638-41) manufactured by Hitachi, Ltd., and Inertsil (registered trademark) $C_{8-3}$ (150×4.6 mm I.D.) as a column were used to perform the analysis by a UV method. As a mobile phase (eluent), a mixed solution (pH 2.8) of 0.1 M $H_3PO_4$ and 0.1 M $NH_4H_2PO_4$ was used. The analysis conditions were as follows: eluent flow rate: 1.0 ml/min, column temperature: 40° C., and detection wavelength: 210 nm. In addition, the sample for liquid chromatography was prepared by mixing 0.5 g of the reaction product (aqueous solution) or the reference standard material with 30 ml of 0.46 M NaOH aqueous solution.

The gas chromatograph was GC-FID (Shimadzu Corporation: GC-14B) and GC-MS (Agilent Technologies: HP-5890, HP-5972), and DB-WAX (60 m: Agilent Technologies) column was used.

The gaseous product collected from the outlet of the ice bath trap was analyzed by using GC-TCD (Shimadzu Corporation: GC-8A, column: Gaskuropack and active carbon) and GC-FID (Shimadzu Corporation: GC-14B, column: DB-WAX).

For the total organic carbon amount, after the liquid product was diluted 500-fold, a total organic carbon analyzer (Total Organic Carbon Analyzer: Shimadzu Corporation) was used to measure the total organic carbon concentration (TOC).

The gas chromatograph and the total organic carbon amount were used for the analysis of byproducts, which is not directly related to the results of experimental example 1, and therefore omitted.

Based on the area ratio of lactic acid and acrylic acid standard solutions in the HPLC chart, the conversion ratio of lactic acid was determined as follows: [1−(area value of lactic acid in product/area value of reference standard material)]× 100, the yield of acrylic acid was determined as follows: (area value of acrylic acid/area value of reference standard material)×100, and the conversion ratio into acrylic acid was determined as follows: (conversion ratio of lactic acid/yield of acrylic acid)×100. In addition, the reference standard material in the case of lactic acid was prepared by adding 30 ml of 0.46 M NaOH aqueous solution to 0.5 g of 38% by mass lactic acid aqueous solution, and the reference standard material in the case of acrylic acid was prepared by adding 30 ml of 0.46 M NaOH aqueous solution to 30.4% by mass acrylic acid aqueous solution.

The results of the case where the reaction was performed for 6 hours are shown in FIG. 1. The total flow amount of lactic acid when the reaction was performed for 6 hours is 2736 μl. In FIG. 1, 1 is $P_2O_5$ supported on silica, 2 is $Ca_{10}(PO_4)_6(OH)_2$, 3 is $Sr_{10}(PO_4)_6(OH)_2$, and 4 is $CaNO_3$ supported on silica.

Based on FIG. 1, the Ca—P based hydroxyapatite had the best yield of acrylic acid, with the amount of the catalyst of 0.4 g resulting in the acrylic acid yield of 37.0%. In addition, the Sr—P based one had the acrylic acid yield of around 20%. For the $P_2O_5$ based one, it was shown that the conversion ratio of lactic acid was high, but the yield of acrylic acid of interest was low. In addition, for the $CaNO_3$ based one, the amount of the catalyst was set to 1.0 g, but both the conversion ratio of lactic acid and the yield of acrylic acid were very low.

Although not shown in FIG. 1, for the $NaNO_3$ supported on active carbon, the amount of the catalyst used of 0.05 g resulted in the conversion ratio of lactic acid of 30.0%, and the yield of acrylic acid of 17.2%. In addition, a similar experiment to the above was performed for the silica gel, used as a support, alone, with the result that although the conversion ratio of lactic acid was high as 66.7%, the yield of acrylic acid was very low as 2.3%.

Experimental Example 2

Effect of Ca/P

Next, an experiment of changing Ca/P in the apatite compound was performed, and the effect was investigated. The use ratio of Ca source and P source in the hydrothermal reaction of experimental example 1 was changed, to synthesize catalysts with Ca/P of 1.5, 1.6, and 1.8.

A synthesis reaction of acrylic acid was performed for 6 hours, in a similar manner to experimental example 1, except that the amount of the catalyst used was 1 g. The $Ca_{10}(PO_4)_6(OH)_2$ with Ca/P of 1.67 showed the highest result, in which the conversion ratio of lactic acid was 91.4% and the yield of acrylic acid was 72.0%. Also, in all the cases of Ca/P of 1.5, 1.6, and 1.8, the yield of acrylic acid was over 50%, and it was enough for a catalytic performance. In addition, a similar experiment was performed for $Sr_{10}(PO_4)_6(OH)_2$, with the amount of the catalyst of 1 g, and it could be confirmed that the conversion ratio was 54.3% and the yield of acrylic acid was 33.6%.

Experimental Example 3

Effect of Amount of Catalyst

Figure 2:
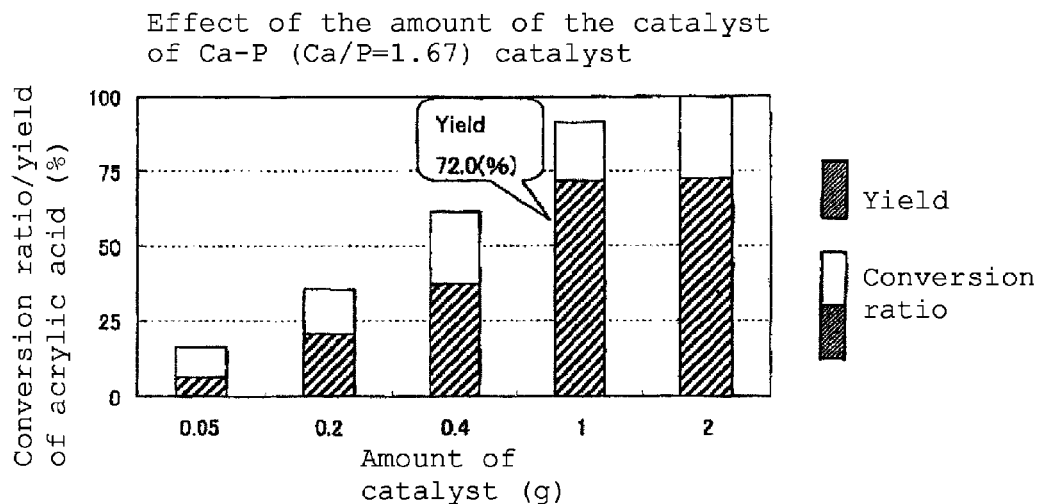
FIG. 2 shows the relationship between the amount of the catalyst, and the conversion ratio from lactic acid to acrylic acid and yield.

Using $Ca_{10}(PO_4)_6(OH)_2$ with Ca/P of 1.67, the amount of the catalyst was changed to investigate its effect. A synthesis reaction of acrylic acid was performed for 6 hours, in a similar manner to experimental example 1, except for changing the amount of the catalyst used. The results are shown in FIG. 2. Both the conversion ratio of lactic acid and the yield of acrylic acid increased along with increase in the amount of the catalyst up to 1 g. When the amount of the catalyst was set to 2 g, the conversion ratio of lactic acid was 100%, but the yield of acrylic acid was very little changed from that of the case of 1 g, and thus the effectiveness of catalyst reached the limit.

Experimental Example 4

Change Over Time

Figure 3:
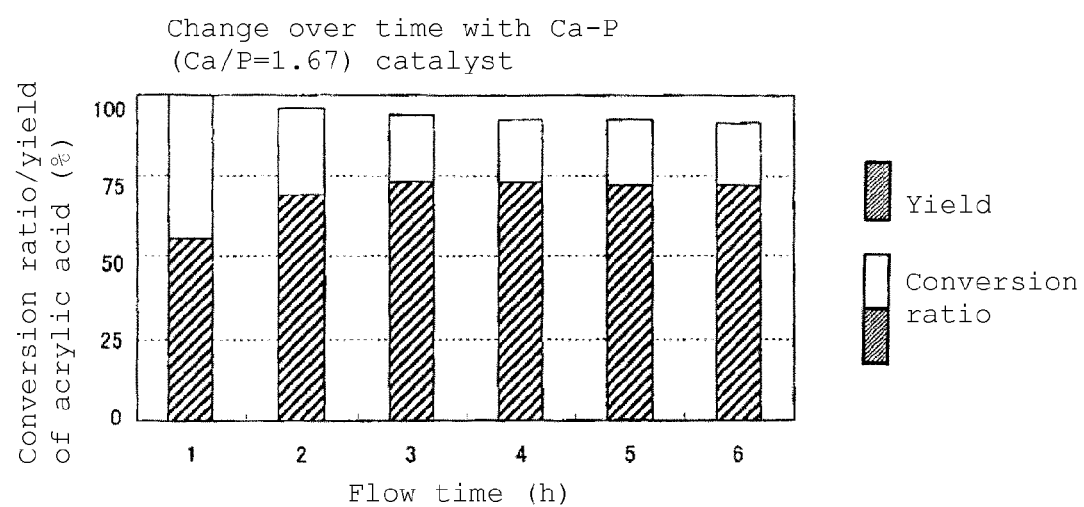
FIG. 3 shows the relationship between flow time, and the conversion ratio from lactic acid to acrylic acid and the yield.

Using 1 g of $Ca_{10}(PO_4)_6(OH)_2$ with Ca/P of 1.67, a synthesis reaction of acrylic acid was performed in a similar manner to experimental example 1, and the condition in every hour was traced. The results have been shown in FIG. 3. It was shown that from the third hour onwards, there was no great change in the yield of acrylic acid.

Experimental Example 5

Change Over Time

Using 1 g of $Ca_{10}(PO_4)_6(OH)_2$ with Ca/P of 1.67, a synthesis reaction of acrylic acid was performed in a similar manner to experimental example 1, and the change over time in 60 hours was traced. It was shown that the conversion ratio of lactic acid did not decrease so much over time, but the selectivity or the yield of acrylic acid gradually decreased. However, the yield of acrylic acid was over 50% even in the case of performing a continuous reaction for 60 hours, and it could be confirmed that the apatite compound based catalyst used in the present invention was durable for long time use.

Experimental Example 6

A synthesis experiment of ethyl acrylate using ethyl lactate as a raw material compound was performed. The reaction was performed for 6 hours, in a similar manner to experimental example 1, except for using ethyl lactate (100%) instead of a lactic acid aqueous solution and using 1 g of $Ca_{10}(PO_4)_6(OH)_2$ with Ca/P of 1.67.

The reaction product was analyzed in a similar manner to experimental example 1. As for GC-MS and GC-FID, the analysis was performed after 10-fold dilution with methanol.

The conversion ratio of ethyl lactate after flowing for 6 hours was 55%, and in the reaction product were comprised ethyl acrylate and acrylic acid. The total yield of them was 18%.

INDUSTRIAL APPLICABILITY

In the method of the present invention, an unsaturated carboxylic acid and/or a derivative thereof can be synthesized from a biomass-derived hydroxycarboxylic acid and/or a derivative thereof in high yield, and therefore it has become possible to synthesize an industrially useful unsaturated carboxylic acid and/or a derivative thereof, without the need for petroleum-derived raw materials.

The invention claimed is:

1. A method for synthesizing an unsaturated carboxylic acid and/or a salt or an ester thereof, wherein an apatite compound is used as a catalyst to synthesize the unsaturated carboxylic acid and/or the salt or the ester thereof from a biomass-derived hydroxycarboxylic acid and/or a salt or an ester thereof by a dehydration reaction, wherein $Ca_{10}(PO_4)_6(OH)_2$ is used as the apatite compound.

2. The synthesis method according to claim 1, wherein the hydroxycarboxylic acid is lactic acid, and the unsaturated carboxylic acid is acrylic acid.

3. A method for synthesizing an unsaturated carboxylic acid and/or a salt or an ester thereof, wherein an apatite compound is used as a catalyst to synthesize the unsaturated carboxylic acid and/or the salt or the ester thereof from a biomass-derived hydroxycarboxylic acid and/or a salt or an ester thereof by a dehydration reaction, wherein a compound represented by the formula: $M_a(M'O_b)_cX_2$ wherein M represents Ca, Sr, Pb, Mg, Cd, Co, Ni, Cu, Zn, La, H, or two or more types of these, M' represents P, V, As, C, S, or a combination thereof, and X represents OH, F, or Cl is used as the apatite compound.

4. The synthesis method according to claim 3, wherein an apatite compound having a molar ratio of M to M' (a/c) of 1.5 to 1.8 is used as the apatite compound.

* * * * *

UNITED STATES PATENT AND TRADEMARK OFFICE
CERTIFICATE OF CORRECTION

PATENT NO.       : 8,772,539 B2  Page 1 of 1
APPLICATION NO.  : 13/503780
DATED            : July 8, 2014
INVENTOR(S)      : Onda et al.

It is certified that error appears in the above-identified patent and that said Letters Patent is hereby corrected as shown below:

In the Claims

Column 8, claim 3, lines 41-42, should read: -- represented by the formula: $M_a(M'O_b)_cX_2$ wherein M represents Ca, Sr, Pb, Mg, Cd, Fe, Co, Ni, Cu, Zn, La, H or two or --

Signed and Sealed this
Ninth Day of December, 2014

Michelle K. Lee
*Deputy Director of the United States Patent and Trademark Office*